United States Patent [19]

DeCoster

[11] Patent Number: Plant 6,337

[45] Date of Patent: Oct. 11, 1988

[54] PHILODENDRON PLANT NAMED IMPERIAL RED

[76] Inventor: Paul DeCoster, Brusselsesteenweg 94, 9230 Melle, Belgium

[21] Appl. No.: 927,608

[22] Filed: Nov. 6, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Schwartz, Jeffery, Schwaab, Mack, Blumenthal & Evans

[57] ABSTRACT

A philodendron plant named Imperial Red particularly characterized by its rosette plant form, relatively large leaves which are generally brown-maroon when immature to dark green-maroon when mature; fast and compact growth habit, and compact form; close and symmetrical internodes, dark green petioles with red-purple sheaths, and by its efficient propagation by tissue culture.

2 Drawing Sheets

The present invention comprises a new and distinct cultivar of philodendron plant named Imperial Red.

The new cultivar was discovered growing among several hundred random seedlings obtained in approximately September of 1977 from Bamboo Nursery, Opapka, Fla. The plants were approximately 3–4" long with roots, but not rooted in soil, and were indistinguishable one from the other at the time of purchase. The parentage of the new cultivar was not known at the time of acquisition, nor is it now known.

When the seedlings were grown to mature plants by applicant in Melle, Belgium, in the greenhouses of applicant, the novel characteristics of Imperial Red were readily evident. Asexual reproduction by me of the new cultivar by tissue culture beginning in approximately 1982 in Melle, Belgium, and repeated asexual reproduction thereafter, has demonstrated that Imperial Red retains its distinctive characteristics through successive propagation.

The following characteristics in combination distinguish Imperial Red from other philodendron cultivars of this general type.

1. A rosette plant form, i.e., self-heading from which leaf stalks develop, in the same manner as in the cultivar Black Cardinal, disclosed in U.S. Plant Pat. No. 5,355, the commercial cultivar Pluto, or the cultivar Imperial Green, disclosed in my pending application.

2. Dark green-maroon, relatively large mature foliage.

3. Propagates very efficiently by tissue culture, a very important characteristic for rosette type philodendrons. The more compact form of rosette types, as compared to the more vertically grown philodendron normally attached to moss poles or the like, makes removal of the meristem difficult. In Imperial Red, such removal can be accomplished relatively easily.

4. Compact growth habit and form, from beginning to maturity, thereby allowing plant to be sold in 4" pots and larger with the same degree of compactness. It is therefore excellent for indoor decorating and outdoor planting.

5. Very close and symmetrical internodes, approximately 1 cm apart, thereby providing the compact form indicated.

6. Fast grower for rosette type, reaching approximately 30–33" in diameter approximately 20" above edge of 25 cm pot in about twelve (12) months, starting from a three (3) month old 10 cm plantlet obtained from tissue culture.

7. In immature plants (plant prior to flowering), leaves are relatively erect and carried on rigid stalks thereby making the plant convenient to wrap and ship.

8. The sheathing around the petioles is an attractive red-purple on the inner surface, with the outer surface being more reddish purple.

9. The buds are oblong and generally red-purple in color. When opening, the outside of the spathe retain the bud color, and the inside of the spathe ranges from light to dark pink. This provides a pleasant contrast with the spadix, which is normally pink.

Imperial Red can be compared with the cultivar Imperial Green, disclosed in my pending application. The main difference between the cultivars is that in Imperial Red, the leaf color is a dark green-maroon. The growth habit of Imperial Red is somewhat slower, and the leaf shape is different, with the face being less concave than in Imperial Green and the overall length somewhat more.

In the color photographic drawings, sheet 1 is a top perspective view of two plants of Imperial Red, approximately ten (10) months old, in a 25 cm pot. Sheet 2 is a side elevational view of the new cultivar, showing more clearly the compact, rosette form. The photographs were taken when the plant was not in flower.

The following observations and measurements are based on plants of Imperial Red twelve (12) months in age grown in Melle, Belgium in greenhouses in accordance with standard commercial practices. Color values are based on The Royal Horticultural Society Colour Chart (R.H.S.), with the color values being taken in mid-September at approximately 10:00 a.m. under natural light conditions.

FORM CHARACTERISTICS

Leaf shape:

*Mature.*—Generally elliptic, with bottom of leaf being mildly concave shaped at petiole connecter; undulating or wavy in direction of length, particularly at edge.

*Immature.*—Generally ovate, with bottom of leaf at petiole connector being essentially a continuous edge.

*Tip.*—Cuspidate.

*Base.*—Concavely shaped relative to rib; auriculate.

*Margin.*—Smooth.

*Venation.*—Present.

Leaf attachment: Stalked.

Leaf arrangement: Alternate.

Petiole: Rigid, extending generally more vertical than horizontal in center of plant; round except flat on inner surface.

Stem: Rosette type, short, heavy internodes relatively close, approximately ½" to 1".

Overall appearance: Self-branching, free-standing, open but compact.

SIZE CHARACTERISTICS OF TYPICAL COMMERCIAL PLANT

Leaf (mature):

*Width at widest point.*—18–19 cm.

*Width 1" from top.*—3–4 cm.

*Length.*—38–40 cm.

Petiole:

*Length.*—25 cm for mature leaves.

*Diameter (center).*—Approximately 1.5 cm.

*Internode spacing.*—1 cm.

Stem diameter: Approximately 3–4 cm.

COLOR CHARACTERISTICS

Leaf:

*Mature.*—Top approximately 147A; under surface 147A-B.

*Immature.*—Very difficult to correlate with color chart; top surface closest to 166A with some infusion of red to give an overall maroon appearance; underside lighter than 166A and infused with green; no corresponding color. Color in transition from immature to mature gradually turns from maroon to more deep green mature; intermediate color also does not appear in color chart. Closest value is 199A although actual color is much deeper and infused with maroon.

*Venation.*—Midrib, closest to 147A; veins, same color.

Stem: 148..

Petiole: When mature 148A, with dark, fine and short striations darker than 147A on both round outer and flat inner surfaces; immature petiole is a mixture of dark green and grayed-red and incapable of precise color description; sheath around petiole varies greatly in exterior color, ranging from approximately 183B for immature petioles to 166A heavily infused with 183B during mature stage prior to petiole dropping. The interior surface of the petiole is generally 183B.

I claim:

1. A new and distinct cultivar of philodendron plant named Imperial Red, as described and illustrated, and particularly characterized by its rosette plant form, relatively large leaves which are generally brown-maroon when immature to dark green-maroon when mature; fast and compact growth habit, and compact form; close and symmetrical internodes, dark green petioles with red-purple sheaths, and by its efficient propagation by tissue culture.

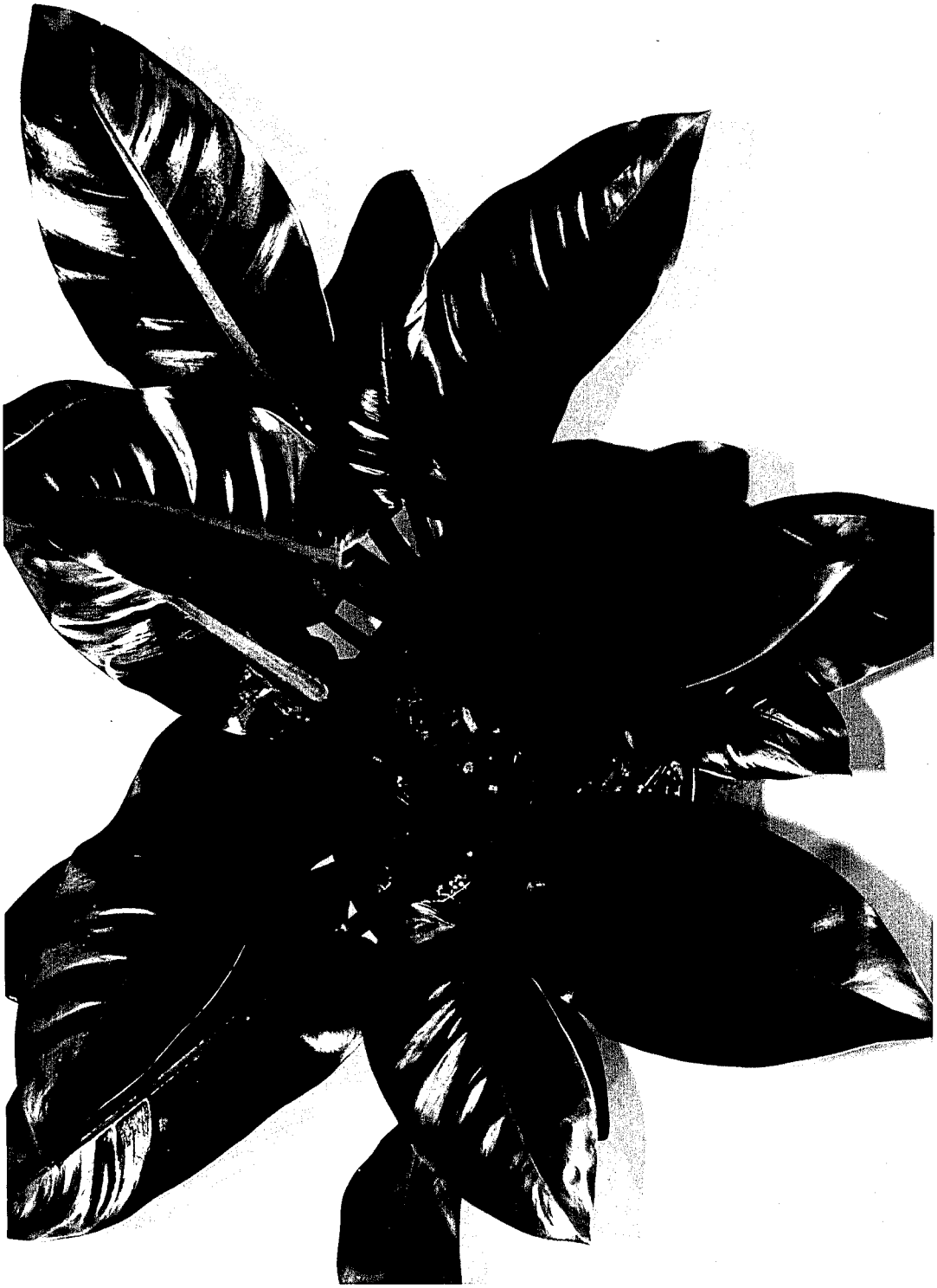

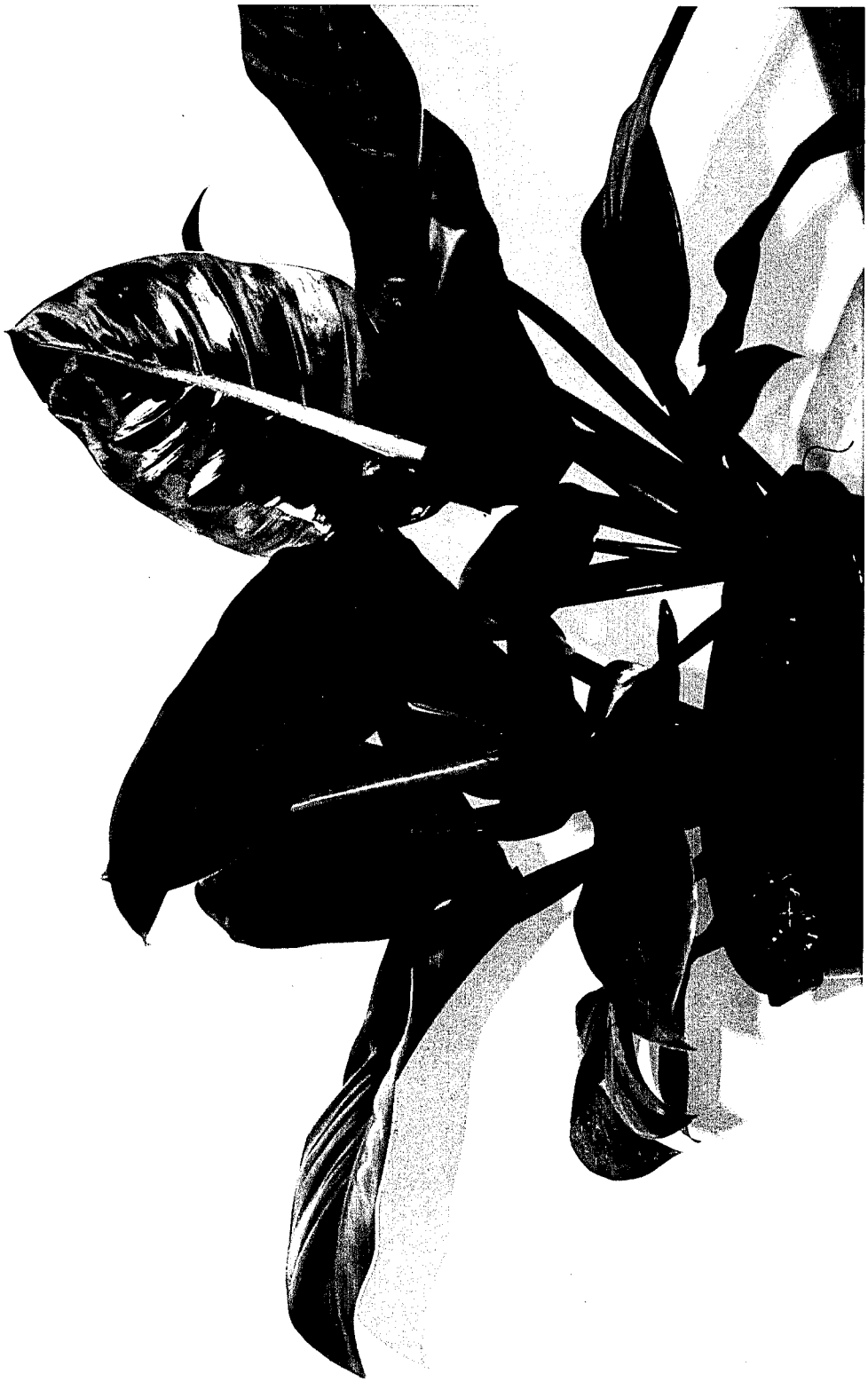

* * * * *